(12) United States Patent
Kang

(10) Patent No.: US 9,936,957 B2
(45) Date of Patent: Apr. 10, 2018

(54) MICRO-COIL ASSEMBLY

(71) Applicant: INCUMEDx, Inc., Fremont, CA (US)

(72) Inventor: Ho Chang Kang, Gyeonggi-do (KR)

(73) Assignee: INCUMEDx, Inc., Fremont, CA (US)

( * ) Notice: Subject to any disclaimer, the term of this patent is extended or adjusted under 35 U.S.C. 154(b) by 332 days.

(21) Appl. No.: 14/291,650

(22) Filed: May 30, 2014

(65) Prior Publication Data

US 2014/0277100 A1    Sep. 18, 2014

Related U.S. Application Data

(63) Continuation of application No. PCT/KR2011/009384, filed on Dec. 6, 2011.

(30) Foreign Application Priority Data

Dec. 2, 2011 (KR) ........................ 10-2011-0128649

(51) Int. Cl.
 *A61B 17/12* (2006.01)

(52) U.S. Cl.
 CPC .... *A61B 17/12113* (2013.01); *A61B 17/1214* (2013.01); *A61B 17/12154* (2013.01); *A61B 2017/12054* (2013.01)

(58) Field of Classification Search
 CPC ............. A61B 17/12; A61B 17/12022; A61B 17/12113; A61B 17/1214–17/12154;
 (Continued)

(56) References Cited

U.S. PATENT DOCUMENTS 5,250,071 A    10/1993 Palermo
5,261,916 A    11/1993 Engelson
(Continued)

FOREIGN PATENT DOCUMENTS

CN    1874739 A    12/2006
EP    1010396 A1    6/2000
(Continued)

OTHER PUBLICATIONS

Japanese Office Action for Japanese Application No. 2014-544636, dated Nov. 5, 2015, 4 pages.
(Continued)

*Primary Examiner* — Ryan J Severson
*Assistant Examiner* — Charles Wei
(74) *Attorney, Agent, or Firm* — Goodwin Procter LLP

(57) ABSTRACT

Disclosed is a micro-coil assembly including a micro-coil unit which is inserted into an aneurysm or other vascular malformation of a patient and prevents inflow of blood by inducing thrombus, a coil pusher unit which is arranged adjacent to the micro-coil unit and delivers the micro-coil unit to the aneurysm or other vascular malformation of the patient, a tensile wire which is relatively movably arranged in the coil pusher unit, a tie which connects the micro-coil unit and the tensile wire, and a tie cutting unit which is arranged adjacent to the coil pusher unit such that at least a part of the tie cutting unit is movable between a setting position for maintaining the tie in a tied state and a cutting position for cutting the tie, and cuts the tie when moved to the cutting position.

19 Claims, 12 Drawing Sheets

(58) Field of Classification Search
CPC ........... A61B 2017/12054; A61B 2017/12095; A61B 2017/0409; A61B 2017/0488; A61F 2/01; A61F 2002/9511; A61F 2002/9517; A61F 2002/011; A61F 2/95–2/97
USPC .......................... 606/200, 213–215, 232, 233
See application file for complete search history.

(56) References Cited

U.S. PATENT DOCUMENTS

| | | | |
|---|---|---|---|
| 5,263,964 | A | 11/1993 | Purdy |
| 5,304,195 | A | 4/1994 | Twyford, Jr. et al. |
| 5,312,415 | A | 5/1994 | Palermo |
| 5,350,397 | A | 9/1994 | Palermo et al. |
| 5,582,619 | A | 12/1996 | Ken |
| 5,725,546 | A | 3/1998 | Samson |
| 5,814,062 | A | 9/1998 | Sepetka et al. |
| 5,911,737 | A | 6/1999 | Lee et al. |
| 5,944,733 | A | 8/1999 | Engelson |
| 6,022,369 | A | 2/2000 | Jacobsen et al. |
| 6,068,644 | A | 5/2000 | Lulo et al. |
| 6,221,066 | B1 | 4/2001 | Ferrera et al. |
| 6,238,415 | B1 | 5/2001 | Sepetka et al. |
| 6,296,622 | B1 | 10/2001 | Kurz et al. |
| 6,478,773 | B1* | 11/2002 | Gandhi ................. A61B 17/12 604/113 |
| 6,551,305 | B2 | 4/2003 | Ferrera et al. |
| 6,562,021 | B1 | 5/2003 | Derbin et al. |
| 6,835,185 | B2 | 12/2004 | Ramzipoor et al. |
| 6,887,235 | B2 | 5/2005 | O'Connor et al. |
| 6,966,892 | B2 | 11/2005 | Gandhi et al. |
| 7,137,990 | B2 | 11/2006 | Hebert et al. |
| 7,198,613 | B2 | 4/2007 | Gandhi et al. |
| 7,255,707 | B2 | 8/2007 | Ramzipoor et al. |
| 7,377,932 | B2 | 5/2008 | Mitelberg et al. |
| 7,422,569 | B2 | 9/2008 | Wilson et al. |
| 7,722,636 | B2 | 5/2010 | Farnan |
| 7,901,444 | B2 | 3/2011 | Slazas |
| 7,942,894 | B2 | 5/2011 | West |
| 7,972,342 | B2 | 7/2011 | Gandhi et al. |
| 7,985,238 | B2 | 7/2011 | Balgobin et al. |
| 8,062,325 | B2 | 11/2011 | Mitelberg et al. |
| 8,328,860 | B2 | 12/2012 | Strauss et al. |
| 8,333,796 | B2 | 12/2012 | Tompkins et al. |
| 8,597,323 | B1 | 12/2013 | Plaza et al. |
| 8,777,964 | B2* | 7/2014 | Onishi ................. A61B 17/0401 600/567 |
| 8,777,978 | B2 | 7/2014 | Strauss et al. |
| 8,795,316 | B2 | 8/2014 | Balgobin et al. |
| 8,940,011 | B2 | 1/2015 | Teoh et al. |
| 8,945,171 | B2 | 2/2015 | Lim |
| 2002/0165569 | A1* | 11/2002 | Ramzipoor ...... A61B 17/12022 606/191 |
| 2005/0149108 | A1 | 7/2005 | Cox |
| 2006/0025802 | A1 | 2/2006 | Sowers |
| 2006/0036281 | A1 | 2/2006 | Patterson et al. |
| 2006/0116714 | A1 | 6/2006 | Sepetka et al. |
| 2006/0276824 | A1 | 12/2006 | Mitelberg et al. |
| 2007/0005081 | A1* | 1/2007 | Findlay, III ........ A61B 17/0467 606/148 |
| 2008/0119887 | A1 | 5/2008 | Que et al. |
| 2008/0132939 | A1* | 6/2008 | Wilson ............. A61B 17/12022 606/200 |
| 2008/0306504 | A1* | 12/2008 | Win ................. A61B 17/12022 606/191 |
| 2009/0270901 | A1 | 10/2009 | Kelleher et al. |
| 2010/0121350 | A1 | 5/2010 | Mirigian |
| 2011/0029012 | A1* | 2/2011 | Tegels ................ A61B 17/0057 606/213 |
| 2011/0087270 | A1* | 4/2011 | Penner ............... A61B 17/0057 606/213 |
| 2011/0092997 | A1* | 4/2011 | Kang ............... A61B 17/12022 606/191 |
| 2013/0261657 | A1 | 10/2013 | Lorenzo |
| 2013/0325054 | A1 | 12/2013 | Watson |
| 2014/0058434 | A1 | 2/2014 | Jones et al. |
| 2014/0058435 | A1 | 2/2014 | Jones et al. |
| 2014/0277078 | A1 | 9/2014 | Slazas et al. |
| 2014/0277085 | A1 | 9/2014 | Mirigian et al. |

FOREIGN PATENT DOCUMENTS

| | | |
|---|---|---|
| EP | 1621149 A1 | 2/2006 |
| EP | 1806106 A2 | 7/2007 |
| EP | 2777545 A2 | 9/2014 |
| JP | 2003-521991 A | 7/2003 |
| JP | 2006-075281 A | 3/2006 |
| JP | 2007-000596 A | 1/2007 |
| JP | 4253717 B2 | 4/2009 |
| SU | 1318235 A1 | 6/1987 |
| WO | WO-01/58366 A1 | 8/2001 |
| WO | WO-2005032337 A2 | 4/2005 |
| WO | WO-2006126417 A1 | 11/2006 |
| WO | WO-2008064206 A2 | 5/2008 |
| WO | WO-2011/046932 A2 | 4/2011 |

OTHER PUBLICATIONS

Russian Office Action for Russian Application No. 2014126806, dated Dec. 10, 2015, 2 pages.
Chinese Office Action for Chinese Application No. 201180076242, dated Mar. 2, 2016, 9 pages.
Russian Decision on Grant for Russian Application No. 2014126806, dated Apr. 27, 2016, 6 pages.
Australian Patent Examination Report No. 1 for Patent Application No. 2011382564, dated Jun. 2, 2016, 3 pages.
Extended European Search Report for EP 11876854.8, dated May 22, 2015, 6 pages.
Written Opinion for International Application No. PCT/KR2011/009384, dated Dec. 3, 2012, 5 pages.
International Search Report for PCT/KR2011/009384, dated Dec. 3, 2012, 4 pages.
Australian Patent Examination Report No. 2 for Patent Application No. 2011382564, dated Nov. 10, 2016, 3 pages.
Chinese Office Action for Chinese Application No. 201180076242, dated Dec. 5, 2016, 8 pages.
Examination Report No. 3 for Australian Patent Application No. 2011382564, dated Mar. 24, 2017, 3 pages.
Notice of Acceptance for Australian Patent Application No. 2011382564, dated May 11, 2017, 3 pages.
Canadian Office Action for Patent Application No. 2,857,471, dated Oct. 4, 2017, 3 pages.

\* cited by examiner

MICRO-COIL ASSEMBLY

CROSS-REFERENCE TO RELATED APPLICATIONS

This application is a continuation of, claims priority to and the benefit of, and incorporates herein by reference in its entirety International Patent Application No. PCT/KR2011/009384, which was filed on Dec. 6, 2011 and which claims priority to and the benefit of Korean Patent Application No. 10-2011-0128649, which was filed on Dec. 2, 2011 in the Korean Intellectual Property Office and the contents of which are also incorporated herein by reference in their entirety.

BACKGROUND

The inventive concept relates to a micro-coil assembly, and more particularly, to a micro-coil assembly which enables a micro-coil unit to be conveniently and accurately separated from the micro-coil assembly so that the micro-coil unit can be precisely inserted in an aneurysm or other vascular malformation of a patient, thereby efficiently meeting a surgical purpose of an operator.

A cerebral aneurysm (i.e., acute subarachnoid hemorrhage) refers to cerebrovascular swelling on the wall of an artery because of congenitally weak cerebral artery or because of arteriosclerosis, bacterial infections, a head wound, brain syphilis, etc. Such a cerebral aneurysm is suddenly developed without an initial symptom, and brings extreme pain during an attack of the cerebral aneurysm. 15% of cases die suddenly, 15% die under medical treatment, and 30% survive after treatment but feel the acute aftereffect. Therefore, the cerebral aneurysm may be a very deadly disease.

A cure for the cerebral aneurysm is divided into an invasive therapy and a non-invasive therapy. Of these, the non-invasive therapy fills the cerebral aneurysm with a micro-coil to induce thrombus, thereby preventing an additional inflow of blood and decreasing risk of a ruptured aneurysm (embolization). The non-invasive therapy has been being widely researched and developed since it can ease the aftereffect due to brain surgery, have advantage of short hospitalization, and so on.

The micro-coil assembly used in the non-invasive therapy roughly includes a micro-coil unit and a coil-pusher unit for delivering the micro-coil unit to an aneurysm of a patient. When the micro-coil unit starts being inserted in the aneurysm, an operator separates the micro-coil unit from the coil-pusher unit. As a method of separating the micro-coil unit from the coil-pusher unit, there are mechanical methods, chemical methods, thermal methods, etc.

Among them, the most convenient and accurate method is the mechanical method. A conventional mechanical method for the separation is achieved by releasing a locking state between a hook provided in an end part of the micro-coil unit and a hook provided in an end part of the coil-pusher unit. However, such a releasing method is not only complicated but also difficult to separate the micro-coil unit from the coil-pusher accurately at a desired position and desired timing.

Accordingly, research and development have to be carried out on a micro-coil assembly in which the micro-coil unit can be conveniently and accurately separated from the coil-pusher unit.

SUMMARY

The present inventive concept is to provide a micro-coil assembly which enables a micro-coil unit to be conveniently and accurately separated from the micro-coil assembly so that the micro-coil unit can be precisely inserted in an aneurysm or other vascular malformation of a patient, thereby efficiently meeting a surgical purpose of an operator.

According to an aspect of the present inventive concept, there is provided a micro-coil assembly including a micro-coil unit which is inserted into an aneurysm or other vascular malformation of a patient and prevents inflow of blood by inducing thrombus, a coil pusher unit which is arranged adjacent to the micro-coil unit and controllably delivers the micro-coil unit to the aneurysm or other vascular malformation of the patient, a tensile wire which is relatively movably arranged in the coil pusher unit, a tie which connects the micro-coil unit and the tensile wire, and a tie cutting unit which is arranged adjacent to the coil pusher unit such that at least a part of the tie cutting unit is movable between a setting position for maintaining the tie in a tied state and a cutting position for cutting the tie, and cuts the tie when moved to the cutting position.

The tie cutting unit may include a first blade which is coupled to the tensile wire and moves linked with a movement of the tensile wire.

The tie cutting unit may further include a second blade which is arranged adjacent to the coil pusher unit and cuts the tie by the interaction with the first blade when the first blade is moved to the cutting position.

The second blade may be fixedly arranged not to move into the coil pusher unit, a second blade passing hole through which the tie passes in a lengthwise direction of the coil pusher unit may be formed in the second blade, and the first blade may be inserted in the second blade passing hole when cutting the tie.

An inner diameter of the second blade passing hole may be greater than an outer diameter of the first blade and less than a sum of the outer diameter of the first blade and a thickness of the tie.

A first blade passing hole through which the tie passes in the lengthwise direction of the coil pusher unit may be formed in the first blade.

The tie may include a first knot part which is knotted at a rear end portion of the tensile wire, a first extension part which is connected to the first knot part and passes through the second blade passing hole and the outside of the first blade, a second extension part which is connected to the first extension part and passes through the first blade passing hole, and a second knot part which is connected to the second extension part and knotted at the rear end portion of the tensile wire adjacent to the first knot part.

The cutting position may be a position where the rear end portion of the first blade contacts a front end portion of the second blade to cut the first extension part.

The second blade may be fixedly arranged at a front end portion of the coil pusher unit, a second blade passing hole through which the tie passes in a lengthwise direction of the coil pusher unit and a second blade crossing hole which is formed in a direction crossing the lengthwise direction of the coil pusher unit and communicates with the second blade passing hole which may be formed in the second blade, the first blade may be arranged to be capable of relatively moving with respect to the second blade, and a first blade passing hole in the lengthwise direction of the coil pusher unit and a first blade crossing hole which is formed in a direction crossing the lengthwise direction of the coil pusher unit and communicates with the second blade passing hole may be formed in the first blade.

The tie may include a first knot part which is knotted at a rear end portion of the tensile wire, a first extension part which is connected to the first knot part and passes through the first blade crossing hole and the second blade passing hole, a second extension part which is connected to the first extension part and passes through the first blade passing hole and the second blade passing hole, and a second knot part which is connected to the second extension part and knotted at the rear end portion of the tensile wire adjacent to the first knot part.

The cutting position may be a position where the first extension part is cut by the interaction of the first blade and the second blade as the first blade moves to block the second blade crossing hole.

Any one of an inner wall forming the first blade crossing hole and an inner wall forming the second blade crossing hole may be inclined to have an inner diameter increasing toward an upper end.

The tensile wire may include a knot part stopper which restricts movement of at least any one of the first knot part and the second knot part.

The micro-coil unit may include a thrombus-leading coil which is inserted in the aneurysm or other vascular malformation of the patient and transformed into a previously determined shape to clot blood, and an expansion-resistive core which is arranged passing through an inside of the thrombus-leading coil, wherein the tie may connect the tensile wire and the expansion-resistive core.

The micro-coil unit may further include a core support member which is coupled to the expansion-resistive core and supports the expansion-resistive core in the thrombus-leading coil.

The coil pusher unit may include a pusher tube in which the tensile wire is accommodated.

A screw pattern may be provided in the pusher tube at a part adjacent to the micro-coil unit, the coil pusher unit may further include a coil stopper which is coupled to a leading end of the screw pattern of the pusher tube, forms an opening through which the tie passes, and prevents the micro-coil unit from moving into the pusher tube during cutting of the tie.

The tie may be a suture, and the tensile wire may be accommodated in the coil pusher unit and an end portion of the tensile wire may be exposed to the outside of the coil pusher unit for an operation of the tensile wire.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF THE EMBODIMENTS

The attached drawings for illustrating embodiments of the inventive concept are referred to in order to gain a sufficient understanding of the inventive concept and the merits thereof.

Hereinafter, the inventive concept will be described in detail by explaining embodiments of the inventive concept with reference to the attached drawings.

Figure 1:
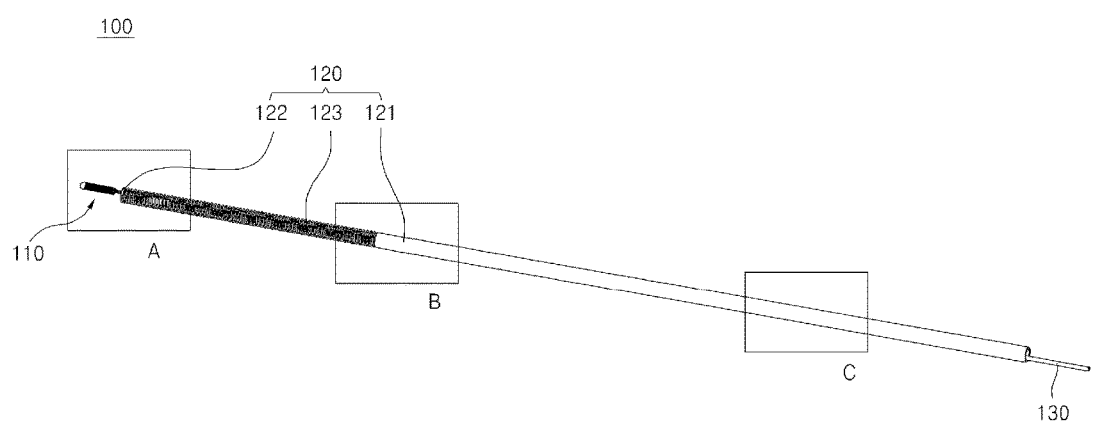
FIG. 1 is a perspective view of a micro-coil assembly according to an exemplary embodiment of the present inventive concept.
Figure 2:
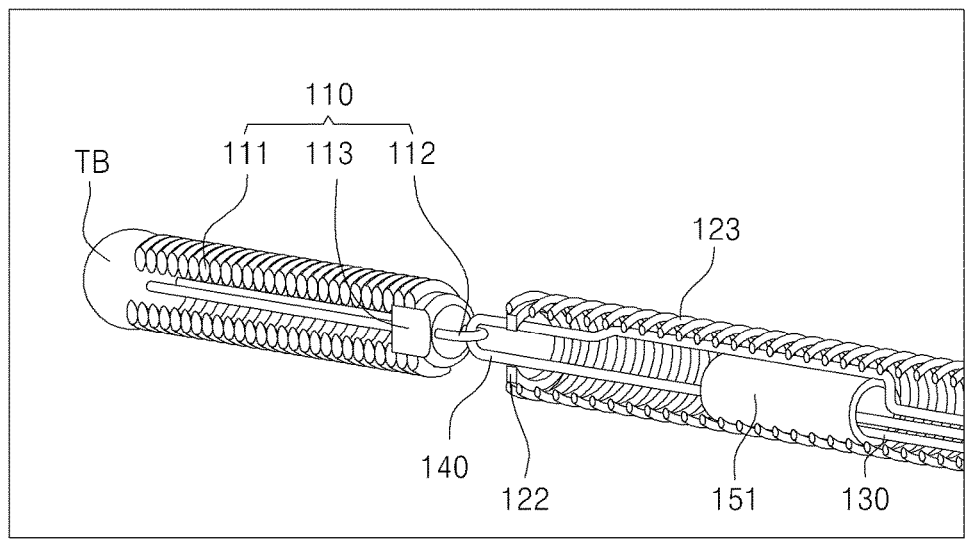
FIG. 2 is an enlarged perspective view of a part A in FIG. 1.
Figure 3:
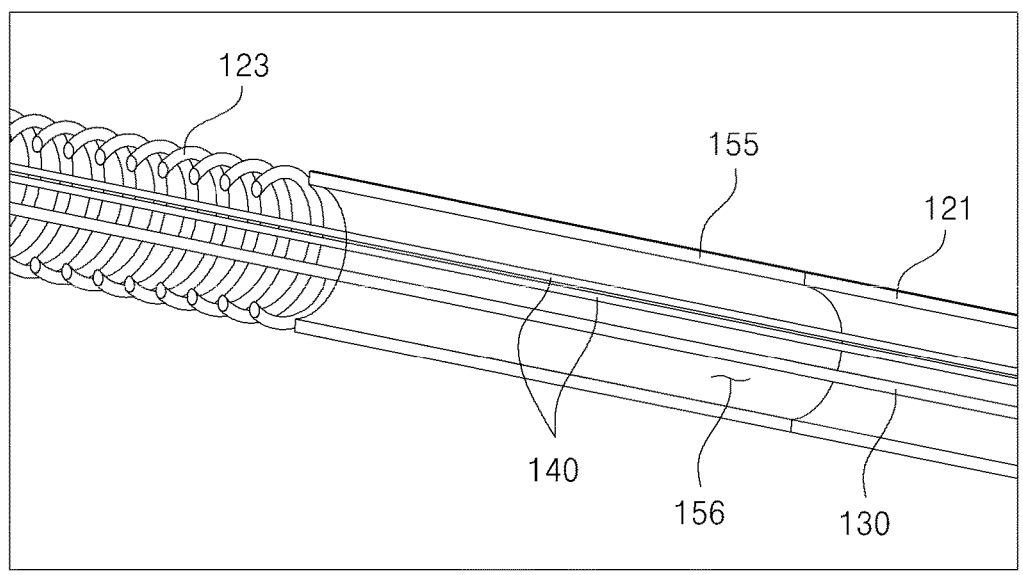
FIG. 3 is an enlarged perspective view of a part B in FIG. 1.
Figure 4:
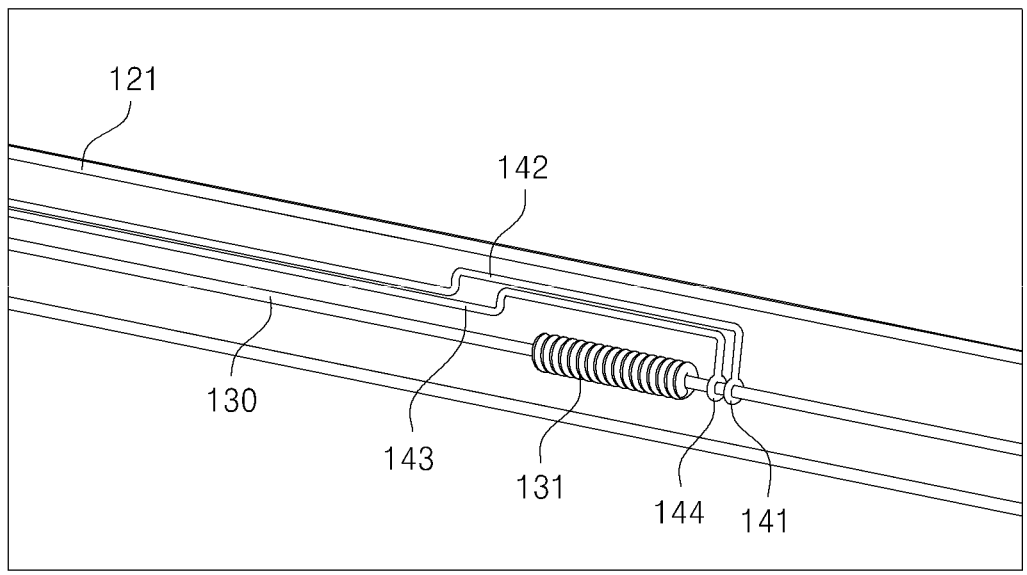
FIG. 4 is an enlarged perspective view of a part C in FIG. 1.
Figure 5:
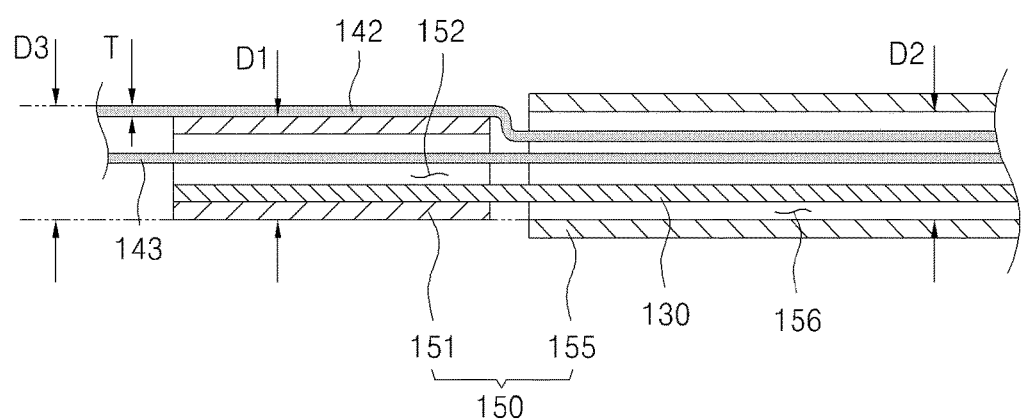
FIG. 5 is a cross-sectional view schematically illustrating the structure of a tie cutting unit in the micro-coil assembly of FIG. 1.
Figure 6:
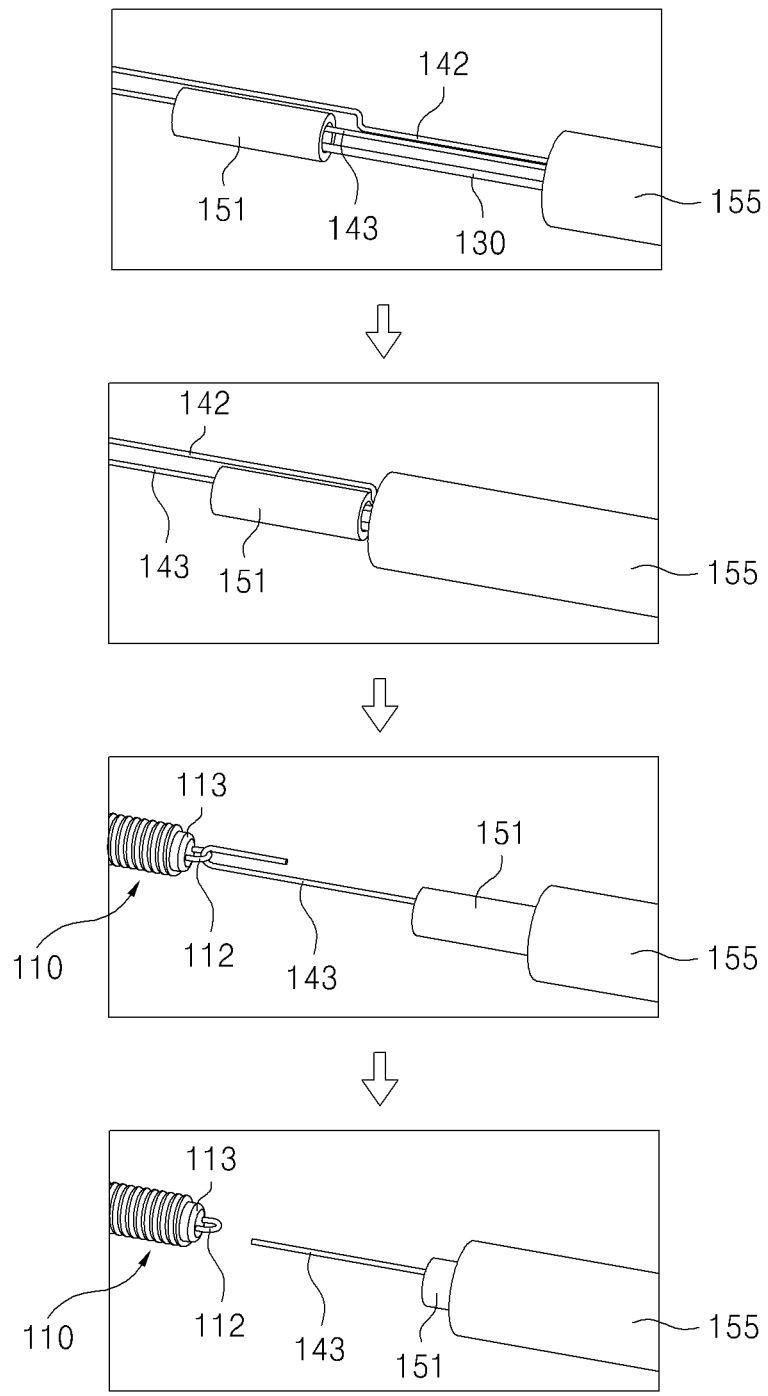
FIG. 6 is a view illustrating a process of cutting a tie in the micro-coil assembly of FIG. 1.
Figure 7:
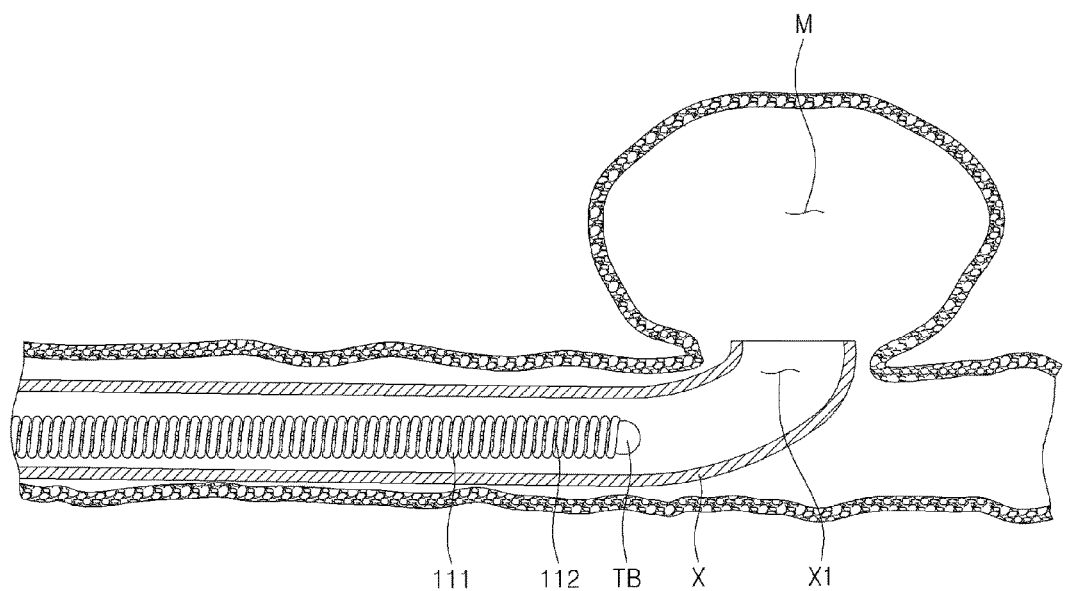
FIG. 7 is a schematic view illustrating that the micro-coil assembly of FIG. 1 is inserted in an arteriovenous malformations aneury of a patient.

FIG. 1 is a perspective view of a micro-coil assembly according to an exemplary embodiment of the present inventive concept. FIG. 2 is an enlarged perspective view of a part A in FIG. 1. FIG. 3 is an enlarged perspective view of a part B in FIG. 1. FIG. 4 is an enlarged perspective view of a part C in FIG. 1. FIG. 5 is a cross-sectional view schematically illustrating the structure of a tie cutting unit in the micro-coil assembly of FIG. 1. FIG. 6 is a view illustrating a process of cutting a tie in the micro-coil assembly of FIG. 1. FIG. 7 is a schematic view illustrating that the micro-coil assembly of FIG. 1 is inserted in an arteriovenous malformations aneury of a patient.

As shown therein, a micro-coil assembly 100 in this embodiment includes a micro-coil unit 110 to be inserted in an aneurysm M or other vascular malformation of a patient to induce thrombus, thereby preventing inflow of blood, a coil pusher unit 120 arranged adjacent to the micro-coil unit 110 and carrying the micro-coil unit 110 to the aneurysm M or other vascular malformation of the patient, a tensile wire 130 arranged in the coil pusher unit 120 to be relatively moveable therein, a tie 140 connecting the micro-coil unit 110 and the tensile wire 130, and a tie cutting unit 150 arranged adjacent to the coil pusher unit 120 such that at least a part thereof can move between a setting position for maintaining the tie 140 in a tied state and a cutting position for cutting the tie 140, and cutting the tie 140 when moved to the cutting position.

The micro-coil unit 110 is inserted into the aneurysm M or other vascular malformation of the patient and induces thrombus, thereby preventing inflow of blood. The micro-coil unit 110 includes a thrombus-leading coil 111 that is changed to a previously determined shape to induce thrombus when inserted in the aneurysm M of the patient, and an expansion-resistive core 112 penetrating the inside of the thrombus-leading coil 111.

The thrombus-leading coil 111 is manufactured by winding a platinum wire having a proper diameter around a coil-winding device (mandrel) and then applying heat treatment to it in a high-temperature oven. Here, the coil-winding device is provided to have a shape corresponding to the shape of the thrombus-leading coil 111 to be transformed in the aneurysm M of a patient. Also, the proper diameter is determined on the basis of the size of a patient's aneurysm M. Alternatively, the diameter of the thrombus-leading coil 111 may be changed on the basis of the shape of the thrombus-leading coil 111 before the transformation, the flexibility of the thrombus-leading coil 111, the shape of the thrombus-leading coil 111 transformed within the aneurysm M, etc.

The expansion-resistive core 112 is changed to have a previously determined shape within the aneurysm M of the patient, so that the thrombus-leading coil 111 can be accurately positioned within the aneurysm M. If the thrombus-leading coil 111 is directly pushed or pulled instead of the expansion-resistive core 112, there may be a gap or close contact between the $N^{th}$ winding part and the $(N+1)^{th}$ winding part of the thrombus-leading coil 111 since thrombus-leading coil 111 is wound spirally.

Accordingly, the expansion-resistive core 112 is provided to solve this problem. An operator (e.g., surgeon or the like) who operates on a patient for the cerebral aneurysm precisely pushes and pulls the expansion-resistive core 112, within the micro-catheter X, so that the thrombus-leading coil 111 connected to the expansion-resistive core 112 can be minutely adjusted. That is, the expansion-resistive core 112 is not easily transformed even when pushed or pulled, so that an operator can accurately insert the thrombus-leading coil 111 in the aneurysm M.

The expansion-resistive core 112 is made of a polymer, which is produced by polymerizing molecules, as being the opposite of a monomer. The expansion-resistive core 112 includes one selected among various kinds of polymers such as polypropylene, nylon, polyamide monofilament, and polyamide composite filament. Polypropylene is a thermoplastic resin produced by polymerizing propylene; nylon is the generic term for a synthesized high molecule polyamide, which refers to a high molecule shaped like a chain connected with —CONH—; the polyamide monofilament is a monofilament provided with polyamide as a polymer having a structure of an aliphatic or aromatic amide backbone; and the polyamide composite filament is a composite filament provided with polyamide.

The expansion-resistive core 112 made of the polymer is not only flexible but also resistive to the expansion, so that it can be advantageously used as a framing coil, a filling coil, or a finishing coil. Here, the framing coil is a coil that is first inserted in the aneurysm M of the patient and provides a frame to be filled with the filling coil; the filling coil is a coil to be filled in the framing coil; and the finishing coil is a coil to be filled in a minute gap of the framing coil not filled with the filling coil.

Alternatively, the expansion-resistive core 112 may be made of Nitinol. The Nitinol is non-magnetic alloy formed by mixing nickel and titanium in approximately the same ratio.

Meanwhile, one end part of the expansion-resistive core 112 adjacent to the coil pusher unit 120 is shaped like a loop, and the other end part thereof is shaped like a ball or a tip-ball (TB) formed by melting or welding part of the expansion-resistive core 112, depending on the type of material used for this component. Specifically, the expansion-resistive core in this embodiment is shaped like double loops each of which has a loop shape and which are spaced apart from each other in a vertical direction.

Like this, the one end part of the expansion-resistive core 112 is shaped like a loop, so that the tie 140 can penetrate the inside of the expansion-resistive core 112 and easily tie the expansion-resistive core 112. Thus, the expansion-resistive core 112 is connected to the tensile wire 130 via the tie 140.

Further, the micro-coil unit 110 further includes a core support member 113 that is connected to the expansion-resistive core 112 and supporting the expansion-resistive core 112 in the thrombus-leading coil 111. The core support member 113 is provided at the opposite side of the tip-ball (TB). As the core support member 113 is provided at the opposite side of the tip-ball (TB) to support the expansion-resistive core 112, the expansion-resistive core 112 is stably arranged in an internal cavity of the thrombus-leading coil 111.

Meanwhile, the other end part of the expansion-resistive core 112 is formed with a tip-ball (TB), so that a wall of an artery can be protected from being injured by the thrombus-leading coil 111 while the thrombus-leading coil 111 is inserted into the aneurysm M of the patient.

The tip-ball (TB) is formed by melting the expansion-resistive core 112 at a temperature equal to or above the melt temperature of the expansion-resistive core 112 material. This can be accomplished by applying heat capable of melting the expansion-resistive core 112 material in the form of convective heated air, conductive heat or heat radiating from a source such as a soldering iron. Alternatively, if a metallic material is used for the expansion-resistive core 112, the tip-ball (TB) may be formed by arc-welding the other end part opposite to the one end part adjacent to the coil pusher unit 120 of the expansion-resistive core 112. Particularly, the tip-ball (TB) in this embodiment is formed by electric arc welding the other end part of the expansion-resistive core 112, in which the electric arc welding process melts the thrombus-leading coil 111 material into a spherical shape. Some metallic materials may require the arc-welding process to be performed in an inert-gas vacuum.

The electric arc welding method is proper to form the tip-ball (TB) of the expansion-resistive core 112 in this embodiment since no coating material is used, no slag is generated, and precise welding is possible. However, the right scope of the present inventive concept is not limited to this method of forming the tip-ball (TB). Alternatively, the tip-ball (TB) in this embodiment may be formed by applying not the electric arc welding but another welding method to the other end of the expansion-resistive core 112.

The thrombus-leading coil 111 is fixed to the expansion-resistive core 112 as one end part thereof is in contact with the tip-ball (TB). Alternatively, the tip-ball (TB) may be provided by applying the arc-welding between one end part of the thrombus-leading coil 111 and one end part of the expansion-resistive core 112. That is, the tip-ball (TB) may be provided by not applying the welding to the other end part of the expansion-resistive core 112 but applying the arc-welding between one end part of the thrombus-leading coil 111 and the other end part of the expansion-resistive core 112.

Yet another method of forming a tip-ball (TB) is to use an adhesive that forms a spherical shape upon application during the manufacturing process and secures the expansion-resistive core 112 to the end of the thrombus leading coil 111. The adhesive would be an implant-grade polymer, such as n-butyl cyanoacrylate or co-polymer such as an epoxy. Depending on the type of adhesive used, the tip-ball (TB) is formed upon curing of the adhesive with ultraviolet light or high-temperature application.

The coil pusher unit 120 is arranged adjacent to the micro-coil unit 110 and carries the micro-coil unit 110 to the aneurysm M of the patient. The coil pusher unit 120 includes a pusher tube 121 in which the tensile wire 130 is accommodated.

The pusher tube 121 may be made of metal alloy such as Nitinol or 300-series stainless steel; a rigid polymer such as polyetheretherketon (PEEK); or a rigid polymer tube formed by mechanically combining the rigid polymer and the metal alloy.

In this embodiment, the pusher tube 121 is provided with a screw pattern 123, which is comprised of a metallic coil laminated with a polymer jacket, making this portion of the pusher tube 121 easy to bend and adjacent to the micro-coil unit 110. The screw pattern 123 provided in the pusher tube 121 may prevent the pusher tube 121 from being abruptly folded at a particular position so that the pusher tube 121 may be smoothly bent. Further, an external protective polymer tube (not shown) may be coupled to an outer surface of the pusher tube 121 having the screw pattern 123.

The screw pattern 123 is intended to make the pusher tube 121 more flexible for smoother navigation into a patient's neurovasculature. An alternative method of making the pusher tube flexible is to create a pattern of multiple adjacent slots cut on either side of the distal section of the solid tube, 180 degrees apart, where each slot is cut to a depth less than half of the tube diameter. Adjacent slots may also alternate from 5 degrees to 90 degrees, such that no preferential bending exists in the pusher tube.

In this embodiment, the coil pusher unit 120 further includes a coil stopper 122 that is coupled to a leading end of the screw pattern 123 of the pusher tube 121, forms an opening through which the tie 140 passes, and prevents the micro-coil unit 110 from moving into the pusher tube 121 during cutting of the tie 140.

The coil stopper 122 facilitates cutting of the tie 140 by restricting the micro-coil unit 110 from moving to the inside of the screw pattern 123 during the cutting of the tie 140.

The tensile wire 130 is arranged to be relatively movable with respect to the coil pusher unit 120. In this embodiment, the tensile wire 130 is arranged in the pusher tube 121 to be capable of relatively moving with respect to the pusher tube 121. Further, for an operation of the tensile wire 130, one end part of the tensile wire 130 is exposed to the outside of the pusher tube 121.

As describe later, the tie 140 is connected to the tensile wire 130 via knots 141 and 144. A knot part stopper 131 for restricting the movements of the knots 141 and 144 is provided on the tensile wire 130, which will be described later for convenience of explanation.

The tie 140 connects the micro-coil unit 110 and the tensile wire 130. As the opposite ends of the tie 140 form knots on the tensile wire 130, the tie 140 connects the micro-coil unit 110 and the tensile wire 130. The arrangement of the tie 140 will be described later for convenience of explanation. The tie 140 in the present embodiment may be a suture.

The tie cutting unit 150 is arranged adjacent to the coil pusher unit 120 such that at least a part thereof can move between the setting position for maintaining the tie 140 in a tied state and the cutting position for cutting the tie 140, and cuts the tie 140 when moved to the cutting position. In this embodiment, the tie cutting unit 150 is arranged adjacent to the coil pusher unit 120.

The tie cutting unit 150 includes a first blade 151 coupled to the tensile wire 130 and moving linked with the movement of the tensile wire 130. The first blade 151 is coupled to an end portion of the tensile wire 130 at one side thereof to move linked with the movement of the tensile wire 130.

As the first blade 151 is linked with the movement of the tensile wire 130, the movement of the tensile wire 130 moves the first blade 151 between the setting position for maintaining the tie 140 in a tied state and the cutting position for cutting the tie 140, in the coil pusher unit 120.

To facilitate cutting of the tie 140 at the cutting position, the tie cutting unit 150 further includes a second blade 155 provided at the coil pusher unit 120 to cut the tie 140 by the interaction of the first blade 151 when the first blade 151 is moved to the cutting position.

The first blade 151 and the second blade 155 may be made of 300-series stainless steel.

In this embodiment, the second blade 155 is fixedly arranged so as not to be moved into the pusher tube 121. Further, the first blade 151 relatively moves in the screw pattern 123 to approach and be separated from the second blade 155.

In this embodiment, the second blade 155 is arranged adjacent to the pusher tube 121 and may be fixedly arranged in the pusher tube 121.

The first blade 151 arranged to be capable of relatively moving with respect to the second blade 155 is moved toward the second blade 155 due to the movement of the tensile wire 130 during the cutting of the tie 140 and cuts the tie 140 by the interaction with the second blade 155. A cutting part of the tie 140 will be described later for convenience of explanation.

A second blade passing hole 156 through which the tie 140 passes in a lengthwise direction of the coil pusher unit 120 is formed in the second blade 155. A first blade passing hole 152 through which the tie 140 passes in a lengthwise direction of the coil pusher unit 120 is formed in the first blade 151. Accordingly, during the cutting of the tie 140, a part of the first blade 151 is inserted into the second blade pass hole 156, thereby facilitating the cutting of the tie 140.

The tie 140 includes a first knot part 141 knotted at the rear end portion of the tensile wire 130, a first extension part 142 connected to the first knot part 141 and passing through the second blade passing hole 156 and the outside of the first blade 151, a second extension part 143 connected to the first extension part 142 and passing through the first blade passing hole 152, and a second knot part 144 connected to the second extension part 143 and knotted at the rear end portion of the tensile wire 130 adjacent to the first knot part 141.

The first extension part 142 passes through the second blade passing hole 156 to be cut by the relative movement of the first and second blades 151 and 155, particularly by passing through the outside of the first blade 151, not the inside of the first blade 151.

Thus, during the cutting of the tie 140, the first and second blades 151 and 155 cut the first extension part 142. Here, the cutting position is a position where the rear end portion of the first blade 151 contacts the front end portion of the second blade 155.

Further, in this embodiment, to facilitate the cutting of the first extension part 142 due to the contact of the rear end portion of the first blade 151 contacts the front end portion of the second blade 155, an inner diameter D2 of the second blade passing hole 156 is greater than an outer diameter D1 of the first blade 151 and less than a length D3 that is a sum of the outer diameter D1 of the first blade 151 and a thickness T of the tie 140.

When the inner diameter D2 of the second blade passing hole 156 is less than the length D3 that is a sum of the outer diameter D1 of the first blade 151 and the thickness T of the tie 140, the rear end portion of the first blade 151 inserted into the second blade passing hole 156 may easily cut the first extension part 142 of the tie 140.

The tensile wire 130 includes the knot part stopper 131 that restricts movement of at least one of the first and second knot parts 141 and 144. In this embodiment, the knot part stopper 131 restricts the first and second knot parts 141 and 144 from sliding along the tensile wire 130 in a direction toward the first blade 151 in a process of pulling the first blade 151 toward the second blade 155 to cut the tie 140.

As such, the micro-coil assembly 100 according to the present embodiment may conveniently and accurately cut the micro-coil unit 110 from the micro-coil assembly 100 by moving the tie cutting unit 150 from the setting position for maintaining the tie 140 in a tied state and to the cutting position for cutting the tie 140 and cutting the tie 140 connecting the micro-coil unit 110 and the tensile wire 130.

The operation of the micro-coil assembly 100 according to the present embodiment will now be described in detail.

The micro-coil assembly 100 is inserted into the aneurysm M on an artery along a cavity X1 of the micro-catheter X extended from a proper insertion starting position such as the femoral region of the patient to the aneurysm M. That is, the micro-catheter X extended to arteriovenous malformations aneury M is first inserted, and then the micro-coil assembly 100 is inserted along the micro-catheter X. The micro-coil assembly 100 is manufactured to have a very small diameter and thus have certain flexibility inside the micro-catheter X, so that it can be conveniently inserted.

The micro-coil unit 110 connected to the coil pusher unit 120 is not randomly deformed within the micro-catheter X according to the stress applied by an inner wall of the micro-catheter X, and is carried as it is to the aneurysm M.

If the micro-coil unit 110 is inserted into the aneurysm M of the patient, the first blade 151 is pulled toward the second blade 155 by pulling the tensile wire 130. Then, the micro-coil unit 110 is restricted from being inserted into the coil pusher unit 120 by the coil stopper 122.

As the first blade 151 is gradually moved toward the second blade 155, the first blade 151 is moved to the cutting position for cutting the tie 140. As the rear end portion of the first blade 151 is engaged with the front end portion of the second blade 155 at the cutting position, the first extension part 142 of the tie 140 is cut.

Next, the tie 140 that is cut is released from the expansion-resistive core 112. As a result, the micro-coil unit 110 is separated from the micro-coil assembly 100.

Since the tie 140 is tied to the tensile wire 130 through the first and second knot parts 141 and 144, even if the tie 140 is cut, the tie 140 is not separated from the tensile wire 130.

As the tie 140 is cut, the micro-coil unit 110 is separated from the micro-coil assembly 100 and is completely inserted in the aneurysm M of the patient.

The micro-coil unit 110, which comes out of the end of the micro-catheter X and is inserted in the aneurysm M, is released from the stress applied by the inner wall of the micro-catheter X, so that the micro-coil unit 10 can be transformed to have a previously determined shape while undergoing the heat treatment, thereby filling the aneurysm M.

The micro-coil unit 110 comes out of the end of the micro-catheter X and is transformed to have a preset random shape such as a two-dimensional spiral shape or a three-dimensional spiral complex pattern. The transformed shape of the micro-coil unit 110 is previously determined depending on the size, the shape and other various data of the aneurysm M of the patient.

In the micro-coil assembly 100 according to this embodiment, as the tie 140 connecting the micro-coil unit 110 and the tensile wire 130 is configured to be cut when the tie cutting unit 140 moving between the setting position and the cutting position moves to the cutting position. Thus, the micro-coil unit 110 is conveniently and accurately separated from the micro-coil assembly 100 and precisely inserted in the aneurysm M of the patient, thereby efficiently meeting a surgical operation of an operator.

Figure 8:
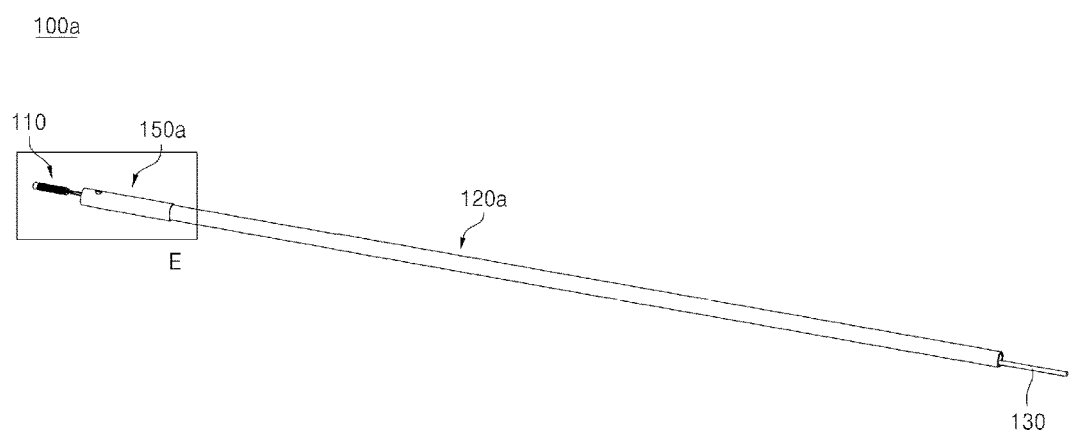
FIG. 8 is a perspective view illustrating a micro-coil assembly according to another exemplary embodiment of the present inventive concept.
Figure 9:
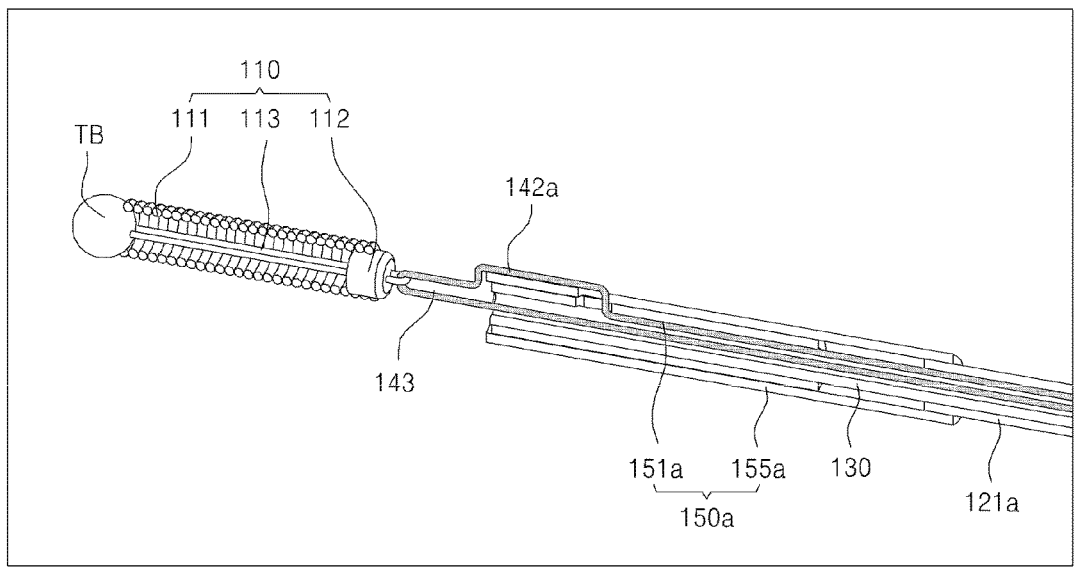
FIG. 9 is an enlarged perspective view illustrating the inside of an area E in FIG. 8.
Figure 10:
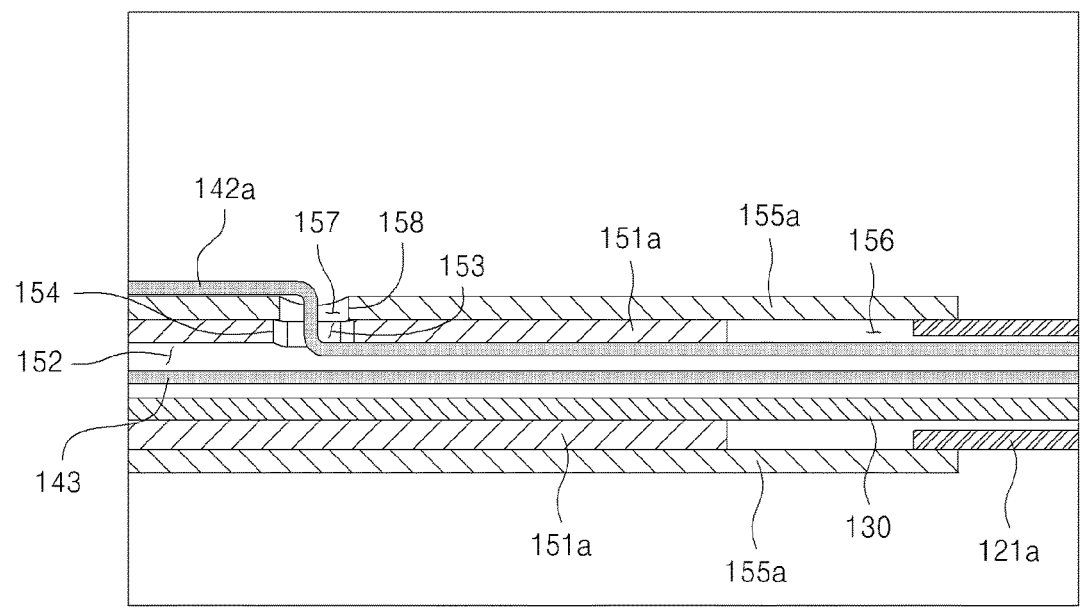
FIG. 10 is a cross-sectional view schematically illustrating the structure of a tie cutting unit in the micro-coil assembly of FIG. 8.
Figure 11:
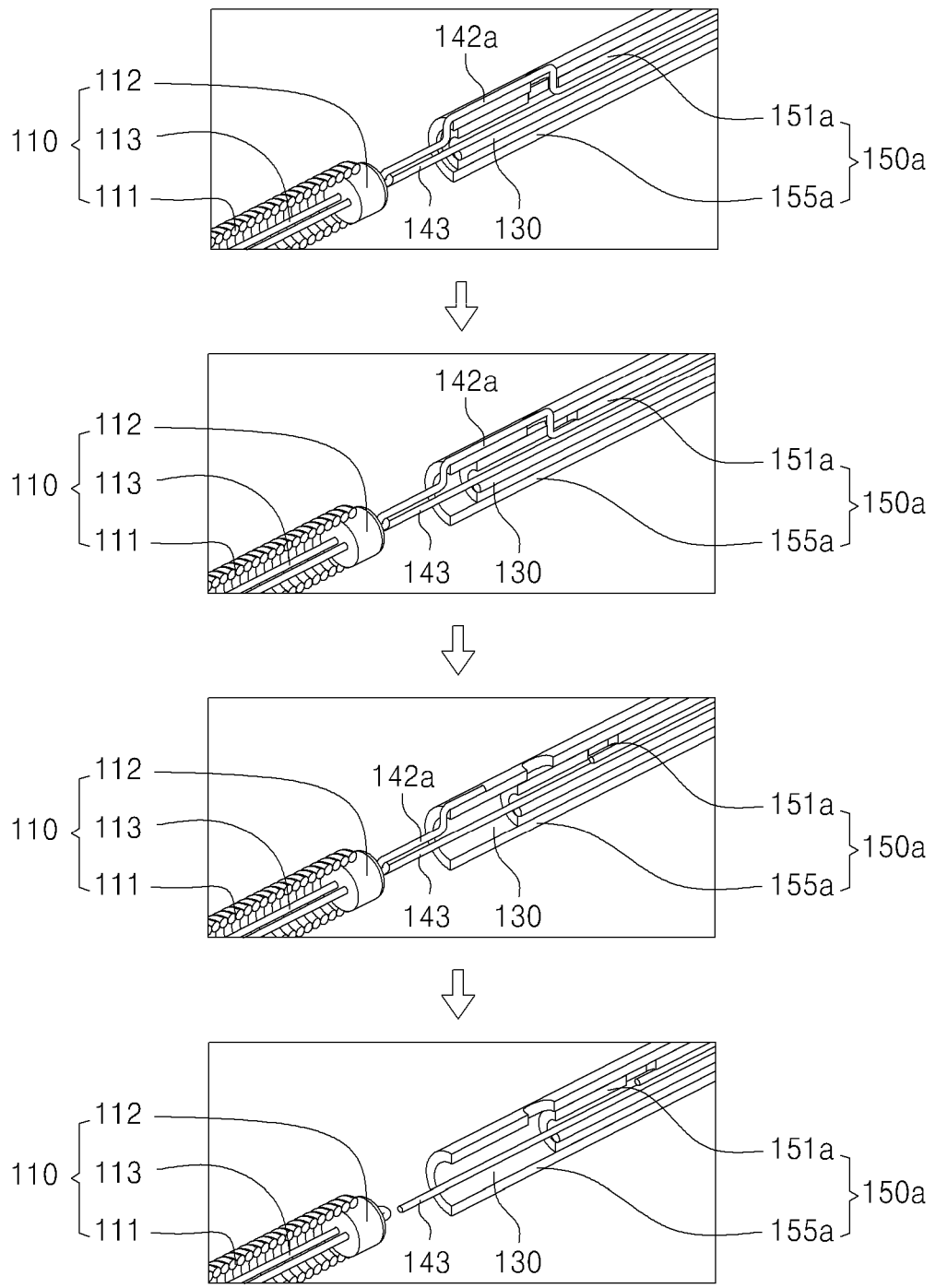
FIG. 11 is a view illustrating a process of cutting a tie in the micro-coil assembly of FIG. 8.

FIG. 8 is a perspective view illustrating a micro-coil assembly 100*a* according to another exemplary embodiment of the present inventive concept. FIG. 9 is an enlarged perspective view illustrating the inside of an area E in FIG. 8. FIG. 10 is a cross-sectional view schematically illustrating the structure of a tie cutting unit in the micro-coil assembly of FIG. 8. FIG. 11 is a view illustrating a process of cutting a tie in the micro-coil assembly of FIG. 8.

In comparison with the first embodiment, the present embodiment is different in the structures of a coil pusher unit 120*a* and a tie cutting unit 150*a* while the other structures are substantially the same as those of the first embodiment of FIGS. 1-7. In the following description, the structures of the coil pusher unit 120*a* and the tie cutting unit 150*a* are mainly discussed.

In the micro-coil assembly 100*a* according to this embodiment, the coil pusher unit 120*a* includes a pusher tube 121*a* having a tube shape in which the tensile wire 130 is accommodated. A second blade 155*a* is fixedly arranged at a front end of the pusher tube 121*a*. As the second blade 155*a* is arranged at the front end of the pusher tube 121*a*, the coil stopper 122 of the first embodiment is not needed so that the structure of the micro-coil assembly 100*a* is simplified.

A second blade passing hole 156 through which a tie 140*a* passes in a lengthwise direction of the coil push unit 120 is formed in the second blade 155*a*, as in the first embodiment.

In this embodiment, a second blade crossing hole 157 is formed in the second blade 155*a*. Unlike the first embodiment, the second blade crossing hole 157 is formed in a direction crossing the lengthwise direction of the coil pusher unit 120 and communicates with the second blade passing hole 156. The second blade crossing hole 157 is formed in a side wall of the second blade 155*a* to communicate with the second blade passing hole 156.

A first blade 151*a* is arranged to be capable of relatively moving with respect to the second blade 155*a*. The first blade 151*a* is moved by being guided along the inside of the second blade 155*a*, that is, by the second blade passing hole 156.

Further, the first blade passing hole 152 is formed in the lengthwise direction of the coil pusher unit 120, as in the first embodiment. A first blade crossing hole 153 is formed in the first blade 151*a*. The first blade crossing hole 153 is formed in the lengthwise direction of the coil pusher unit 120 and communicates with the second blade crossing hole 157 at the setting position, unlike the first embodiment. The first blade crossing hole 153 is formed in a side wall of the first blade 151*a* to communicate with the first blade passing hole 152.

The tie 140*a* includes a first knot part (not shown) knotted at the rear end portion of the tensile wire 130, a first extension part 142*a* connected to the first knot part and passing through the first blade crossing hole 153 and the second blade crossing hole 157, the second extension part 143 connected to the first extension part 142*a* and passing through the first blade passing hole 152 and the second blade passing hole 156, and a second knot part (not shown)

connected to the second extension part 143 and knotted at the rear end portion of the tensile wire 130 adjacent to the first knot part 141.

In this embodiment, the first extension part 142a passes through the first blade crossing hole 153 and the second blade crossing hole 157 to be cut by the relative movement of the first and second blades 151a and 155a.

Consequently, the cutting position for cutting the tie 140a is a position where the first extension part 142a is cut by the interaction of the first and second blades 151a and 155a as the first blade 151a moves to block the second blade crossing hole 157.

At the cutting position, the tie 140a is cut as an inner wall 154 of the first blade crossing hole 153 is engaged with an inner wall 158 of the second blade crossing hole 157.

Figure 12:
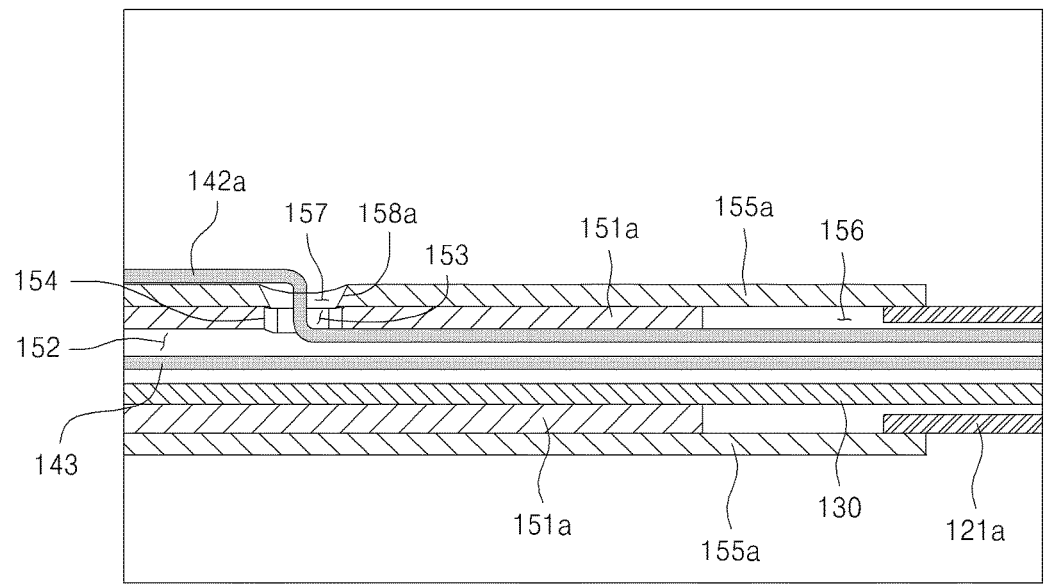
FIG. 12 is a cross-sectional view schematically illustrating the structure of a tie cutting unit in a micro-coil assembly according to another exemplary embodiment of the present inventive concept.

FIG. 12 is a cross-sectional view schematically illustrating the structure of a tie cutting unit in a micro-coil assembly according to another exemplary embodiment of the present inventive concept. In comparison with the second embodiment, the present embodiment is different in the shape of an inner wall 158a of the second blade crossing hole 157 while the other structures are substantially the same as those of the second embodiment of FIGS. 8-11. In the following description, the shape of an inner wall 158a of the second blade crossing hole 157 are mainly discussed.

In the second embodiment, if any one of the inner wall 154 forming the first blade crossing hole 153 and the inner wall 158 forming the second blade crossing hole 157 is inclined with an inner diameter thereof increasing toward an upper end thereof, the cutting of the first extension part 142a is made easy.

Therefore, in this embodiment, the inner wall 158a forming the second blade crossing hole 157 is inclined with an inner diameter thereof increasing toward an upper end thereof.

The first extension part 142a is more easily cut as the inner wall 158a which is inclined with an inner diameter thereof increasing toward an upper end thereof so as to have sharp shape is engaged with the inner wall 154 of the first blade crossing hole 153.

As described above, in the micro-coil assembly according to the present embodiment, the micro-coil unit may be conveniently and accurately separated from the micro-coil assembly by moving the tie cutting unit from the setting position for maintaining the tie in a tied state and to the cutting position for cutting the tie and cutting the tie connecting the micro-coil unit and the tensile wire.

While the inventive concept has been particularly shown and described with reference to exemplary embodiments thereof, it will be understood that various changes in form and details may be made therein without departing from the spirit and scope of the following claims.

What is claimed is:

1. A micro-coil assembly comprising:
a micro-coil unit insertable into a vascular malformation of a patient;
a coil pusher unit for delivering the micro-coil unit to the vascular malformation;
a tensile wire movably arranged within the coil pusher unit;
a tie coupling the micro-coil unit to the tensile wire, the tie being directly connected to the tensile wire; and
a tie cutting unit comprising first and second blades, the first blade comprising at a distal end thereof a first blade passing hole through which the tie passes in a lengthwise direction along a long axis of the first blade, the first blade coupled to the tensile wire and being movable by movement of the tensile wire between a setting position for maintaining the tie in a tied state and a cutting position for cutting the tie, the second blade arranged to cut the tie by interaction with the first blade when the first blade is moved to the cutting position.

2. The micro-coil assembly according to claim 1, wherein the second blade is fixedly arranged in the coil pusher unit,
a second blade passing hole through which the tie passes in a lengthwise direction of the coil pusher unit is formed in the second blade, and
the first blade is insertable into the second blade passing hole to cut the tie.

3. The micro-coil assembly according to claim 2, wherein a diameter of the second blade passing hole is greater than an outer diameter of the first blade and less than a sum of the outer diameter of the first blade and a thickness of the tie.

4. The micro-coil assembly according to claim 2, wherein the tie comprises:
a first knot part knotted at a rear end portion of the tensile wire;
a first extension part coupled to the first knot part and passing through the second blade passing hole and outside of the first blade;
a second extension part coupled to the first extension part and passing through the first blade passing hole; and
a second knot part coupled to the second extension part and knotted at the rear end portion of the tensile wire in proximity to the first knot part.

5. The micro-coil assembly according to claim 4, wherein the cutting position is a position where a rear end portion of the first blade contacts a front end portion of the second blade, thereby cutting the first extension part.

6. The micro-coil assembly according to claim 4, wherein the tensile wire comprises a knot part stopper for restricting movement of at least one of the first knot part and the second knot part.

7. The micro-coil assembly according to claim 1, wherein the second blade is fixedly arranged at a front end portion of the coil pusher unit,
the second blade forms a second blade passing hole through which the tie passes in a lengthwise direction of the coil pusher unit and a second blade crossing hole through which the tie passes in a direction crossing the lengthwise direction of the coil pusher unit and which communicates with the second blade passing hole,
the first blade is movable relative to the second blade, and
the first blade forms a first blade crossing hole through which the tie passes in a direction crossing the lengthwise direction of the coil pusher unit and which communicates with the first blade passing hole.

8. The micro-coil assembly according to claim 7, wherein the tie comprises:
a first knot part knotted at a rear end portion of the tensile wire;
a first extension part coupled to the first knot part and passing through the second blade passing hole, the first blade crossing hole, and the second blade crossing hole;
a second extension part coupled to the first extension part and passing through the first blade passing hole and the second blade passing hole; and
a second knot part coupled to the second extension part and knotted at the rear end portion of the tensile wire in proximity to the first knot part.

9. The micro-coil assembly according to claim 8, wherein the cutting position is a position where the first blade has moved to block the second blade crossing hole, thereby cutting the first extension part.

10. The micro-coil assembly according to claim 7, wherein at least one of an inner wall forming the first blade crossing hole and an inner wall forming the second blade crossing hole is inclined to have an inner diameter increasing toward an upper end.

11. The micro-coil assembly according to claim 1, wherein the micro-coil unit comprises:
    a thrombus-leading coil insertable into the vascular malformation and transformable into a previously determined shape; and
    an expansion-resistive core passing through an inside of the thrombus-leading coil,
    wherein the tie couples the tensile wire to the expansion-resistive core.

12. The micro-coil assembly according to claim 11, wherein the micro-coil unit further comprises a core support member coupled to the expansion-resistive core and that supports the expansion-resistive core in the thrombus-leading coil.

13. The micro-coil assembly according to claim 1, wherein the coil pusher unit comprises a pusher tube within which the tensile wire is movably arranged.

14. The micro-coil assembly according to claim 13, wherein a portion of the pusher tube in proximity to the micro-coil unit comprises a screw pattern, and
    the coil pusher unit further comprises a coil stopper coupled to a leading end of the screw pattern of the pusher tube, the coil stopper forming an opening through which the tie passes and for preventing the micro-coil unit from moving into the pusher tube during cutting of the tie.

15. The micro-coil assembly according to claim 1, wherein the tie comprises a suture.

16. A method for delivering a micro-coil unit to a vascular malformation of a patient, the method comprising:

(i) advancing a micro-coil assembly through a microcatheter to the vascular malformation, the micro-coil assembly comprising:
    the micro-coil unit;
    a coil pusher unit;
    a tensile wire movably arranged within the coil pusher unit;
    a tie coupling the micro-coil unit to the tensile wire, the tie being directly connected to the tensile wire; and
    a tie cutting unit comprising first and second blades, the first blade comprising at a distal end thereof a first blade passing hole through which the tie passes in a lengthwise direction along a long axis of the first blade, the first blade coupled to the tensile wire and being a movable portion of the tie cutting unit, and the second blade being stationary relative to the coil pusher unit; and (ii) cutting the tie by moving the first blade, via the tensile wire, from a setting position in which the tie is maintained in a tied state to a cutting position in which the first blade interacts with the second blade to cut the tie, thereby releasing the micro-coil unit from the tensile wire of the micro-coil assembly and into the vascular malformation.

17. The method of claim 16, wherein moving the first blade to the cutting position comprises pulling on the tensile wire.

18. The method of claim 16, wherein the micro-coil unit comprises a thrombus-leading coil and wherein the method further comprises the step of transforming the thrombus-leading coil into a previously determined shape to induce thrombus after being released into the vascular malformation.

19. The method of claim 18, wherein the previously determined shape comprises at least one of a two-dimensional spiral shape and a three-dimensional spiral complex pattern.

* * * * *